United States Patent
Wouters et al.

(10) Patent No.: US 9,579,329 B2
(45) Date of Patent: Feb. 28, 2017

(54) USE OF ESTETROL AS EMERGENCY CONTRACEPTIVE

(75) Inventors: Wout Wouters, MH Putten (NL); Herman Jan Tijmen Coelingh Bennink, MK Werkhoven (NL); Ludivine Petit, Embourg (BE); Jean-Michel Foidart, Foret Trooz (BE)

(73) Assignee: Estetra S.P.R.L., Bierset (BE)

( * ) Notice: Subject to any disclaimer, the term of this patent is extended or adjusted under 35 U.S.C. 154(b) by 0 days.

(21) Appl. No.: 14/238,310

(22) PCT Filed: Aug. 9, 2012

(86) PCT No.: PCT/EP2012/065572
§ 371 (c)(1),
(2), (4) Date: Feb. 11, 2014

(87) PCT Pub. No.: WO2013/021025
PCT Pub. Date: Feb. 14, 2013

(65) Prior Publication Data
US 2014/0200202 A1    Jul. 17, 2014

Related U.S. Application Data

(60) Provisional application No. 61/522,480, filed on Aug. 11, 2011.

(30) Foreign Application Priority Data

Aug. 11, 2011 (EP) .................................... 11177266

(51) Int. Cl.
*A61K 31/565*    (2006.01)
(52) U.S. Cl.
CPC .................................. *A61K 31/565* (2013.01)
(58) Field of Classification Search
CPC .................................................. A61K 31/565
See application file for complete search history.

(56) References Cited

U.S. PATENT DOCUMENTS

| 7,732,430 B2 * | 6/2010 | Bunschoten et al. ......... 514/169 |
| 7,871,995 B2 * | 1/2011 | Bunschoten et al. ......... 514/171 |
| 2004/0192620 A1 * | 9/2004 | Bunschoten et al. ........... 514/26 |
| 2005/0032755 A1 * | 2/2005 | Van Look et al. ............ 514/170 |

FOREIGN PATENT DOCUMENTS

WO    WO 2004/041839 A2    5/2004

OTHER PUBLICATIONS

Bennick et al., 9th European Congress of Endocrinology Meeting Abstract No. S16.2 (Budapest, Hungary), Endocrine Abstracts, vol. 14 (Apr. 2007).*
Coelingh Bennink et al., Climacteric 11, 47-58 (2008).*
International Search Report and Written Opinion for Application No. PCT/EP2012/065572 mailed Nov. 15, 2012.
International Preliminary Report on Patentability for Application No. PCT/EP2012/065572 mailed Oct. 9, 2013.
Coelingh Bennink et al., Ovulation inhibition by estetrol in an in vivo model. Contraception. Mar. 2008;77(3):186-90. doi:10.1016/j.contraception.2007.11.014. Epub Jan. 22, 2008.
Erkkola et al., Role of progestins in contraception. Acta Obstet Gynecol Scand. Mar. 2005;84(3):207-16.
Fine, Update on emergency contraception. Adv Ther. Feb. 2011;28(2):87-90. doi: 10.1007/s12325-010-0090-x. Epub Dec. 10, 2010.
Visser et al., Clinical applications for estetrol. J Steroid Biochem Mol Biol. Mar. 2009;114(1-2):85-9. doi: 10.1016/j.jsbmb.2008.12.013. Epub Jan. 9, 2009.

* cited by examiner

*Primary Examiner* — Theodore R West
(74) *Attorney, Agent, or Firm* — Wolf, Greenfield & Sacks, P.C.

(57) ABSTRACT

The present invention relates to a new use of tetrahydroxylated estrogens such as estetrol (1,3,5(10)-estratrien-3, 15α, 16α, 17β-tetrol), namely in a method of emergency contraception. The method of emergency contraception according to the invention comprises the oral administration of estetrol in a single dose within 120 hours of sexual intercourse.

12 Claims, 3 Drawing Sheets

USE OF ESTETROL AS EMERGENCY CONTRACEPTIVE

RELATED APPLICATIONS

This application is a national stage filing under 35 U.S.C. §371 of International Application No. PCT/EP2012/065572 filed Aug. 9, 2012, which was published under PCT Article 21(2) in English, and which claims the benefit of European Application No. 11177266.1, filed Aug. 11, 2011 and U.S. Provisional Application No. 61/522,480, filed Aug. 11, 2011, both entitled "USE OF ESTETROL AS EMERGENCY CONTRACEPTIVE", the entire contents of each of which are incorporated by reference herein.

FIELD OF THE INVENTION

The present invention relates to a new use of the known medicinal compound estetrol (1,3,5(10)-estratrien-3, 15α, 16α, 17β-tetrol), namely in a method of emergency contraception.

BACKGROUND OF THE INVENTION

Despite the availability of highly effective methods of contraception, a great number of pregnancies are unplanned, e.g. as a result of lack of access to contraceptives or contraceptive failure (such as condom slippage).

Emergency contraception (EC), by using a drug or device, is an important means of preventing unwanted pregnancy following sexual intercourse. Several approaches to emergency contraception have been described. Although the copper intrauterine device is the most effective EC method that can be used up to 5 days after the estimated time of ovulation, its widespread use is limited due to logistic and medical reasons. In the late 1970s Yuzpe introduced a regimen involving the combined use of oestrogen (0.1 mg ethinylestradiol) and progestogen (0.5 mg levonorgestrel) within 72 hours of the intercourse and repeated after 12 hours. The Yuzpe regimen was associated with a high incidence of nausea and vomiting due to the high oestrogen content. Since 1990s the potential of levonorgestrel (LNG), a synthetic progestogen, was recognised. Treatment with 0.75 mg LNG, repeated after 12 hours or as a single dose of 1.5 mg, within 72 hours of intercourse was shown to be associated with lower rate of side effects and higher efficacy than the Yuzpe regimen. However, if given when luteinizing hormone has already started to rise (LH surge), LNG lacks efficacy. The progesterone receptor modulator mifepristone (10 mg) offers another option for EC with very low side-effects and higher efficacy than the Yuzpe regimen. Also the interval between coitus and treatment could be extended to 120 hours with mifepristone. Yet another regimen is the treatment with the progesterone receptor modulator ulipristal acetate, which is more effective than LNG and which can be used up to 120 hours after intercourse.

There remains a need in the art for alternative methods of emergency contraception with reduced side-effects, which are effective in preventing unwanted pregnancy following intercourse, and which can be administered in a single effective dose, up to 120 hours after the intercourse.

The present invention now provides a new emergency contraceptive overcoming the above posed problems at least partially.

SUMMARY OF THE INVENTION

The present invention provides a new emergency contraceptive, comprising estetrol, a natural estrogen, produced by the human fetal liver during pregnancy only. Structurally, estetrol is characterized by the presence of four hydroxyl groups. In the past, estetrol was considered as a weak estrogen because of its relatively low affinity to estrogen receptors. However, recent studies in rats showed high oral absorption and bioavailability, which resulted in a renewed interest in estetrol. Recent studies support its potential use in applications such as hormone replacement therapy, contraception, prevention of osteoporosis and treatment of breast cancer, but never its use in emergency contraception.

In one aspect the present invention thus provides an emergency contraceptive comprising tetrahydroxylated estrogen represented by the general formula (I):

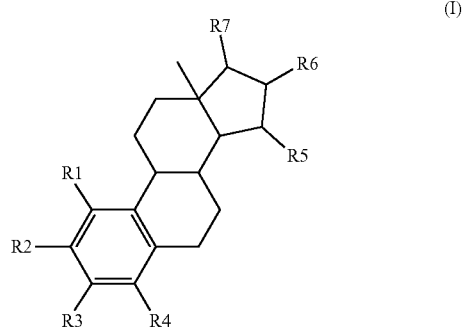

wherein R1, R2, R3, R4 independently are a hydrogen atom, a hydroxyl group, an alkoxy group with 1-5 carbon atoms, or a keto group, preferably wherein R1, R2, R3, R4 independently are a hydrogen atom, a hydroxyl group or an alkoxy group with 1-5 carbon atoms; wherein each of R5, R6, R7 is a hydroxyl group; and wherein no more than 3 of R1, R2, R3, R4 are hydrogen atoms, in an effective amount to inhibit ovulation and/or pregnancy in a female mammal, and a pharmaceutically acceptable salt or excipient.

In a preferred embodiment, the tetrahydroxylated estrogen comprised in the emergency contraceptive as disclosed herein is estetrol (1,3,5(10)-estratrien-3, 15α, 16α, 17β-tetrol).

In a preferred embodiment, the emergency contraceptive as disclosed herein comprises a tetrahydroxylated estrogen in a dose of between 0.5 and 7 mg/kg.

In another embodiment the emergency contraceptive as disclosed herein further comprises an additional active ingredient suitable for preventing pregnancy.

Another aspect of the present invention provides for the use of an emergency contraceptive as taught herein for preventing ovulation.

Yet another aspect of the present invention provides for the use of an emergency contraceptive as taught herein for preventing pregnancy.

Still another aspect of the present invention encompasses a method for preventing ovulation and/or pregnancy in a mammalian female comprising the administration of the emergency contraceptive as disclosed herein in an effective amount to inhibit ovulation and/or pregnancy.

In a preferred embodiment of the method disclosed herein, the administration of the emergency contraceptive as disclosed herein is performed through oral, parenteral, vaginal, rectal, transcutaneous or topical administration. More preferably, said administration is done non-vaginally. Most preferably, said administration is done through oral, parenteral, rectal, transcutaneous or topical administration.

In a further preferred embodiment of the method disclosed herein, the administration of the emergency contraceptive as disclosed herein is performed in a single dosage.

In another preferred embodiment, the administration of the emergency contraceptive as disclosed herein is performed in a double dosage, e.g. with an interval of 6, 12, 18, or 24 hours.

In a further preferred embodiment, the administration of the emergency contraceptive as disclosed herein is performed within 120 hours after sexual intercourse, preferably within 96, 72, 48, 24, 12 hours or less.

Still another aspect of the present invention provides for a pharmaceutical composition for use in a method of emergency contraception in mammalian females, which method comprises the oral, parenteral, vaginal, rectal, transcutaneous or topical administration of a tetrahydroxylated estrogen represented by the general formula (I):

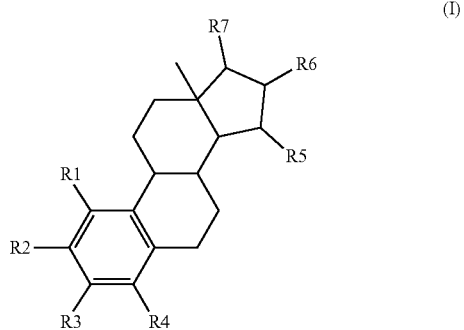

(I)

wherein R1, R2, R3, R4 independently are a hydrogen atom, a hydroxyl group, an alkoxy group with 1-5 carbon atoms, or a keto group, preferably wherein R1, R2, R3, R4 independently are a hydrogen atom, a hydroxyl group or an alkoxy group with 1-5 carbon atoms; wherein each of R5, R6, R7 is a hydroxyl group; and wherein no more than 3 of R1, R2, R3, R4 are hydrogen atoms, to a female of childbearing capability in an effective amount to inhibit ovulation and/or pregnancy and wherein the method encompasses the administration of a single dose of said estrogen to said subject within 120 hours after sexual intercourse.

Preferably, said pharmaceutical composition comprises estetrol (1,3,5(10)-estratrien-3, 15α, 16α, 17β-tetrol).

In another embodiment, said pharmaceutical composition further comprising an additional active ingredient.

Yet another aspect of the present invention encompasses a kit comprising the emergency contraceptive as disclosed herein or the pharmaceutical composition as disclosed herein, and instructions for use.

BRIEF DESCRIPTION OF THE FIGURES

The present invention is illustrated by the following figures which are to be considered for illustrative purposes only and in no way limit the invention to the embodiments disclosed therein.

DETAILED DESCRIPTION OF THE INVENTION

Figure 1:
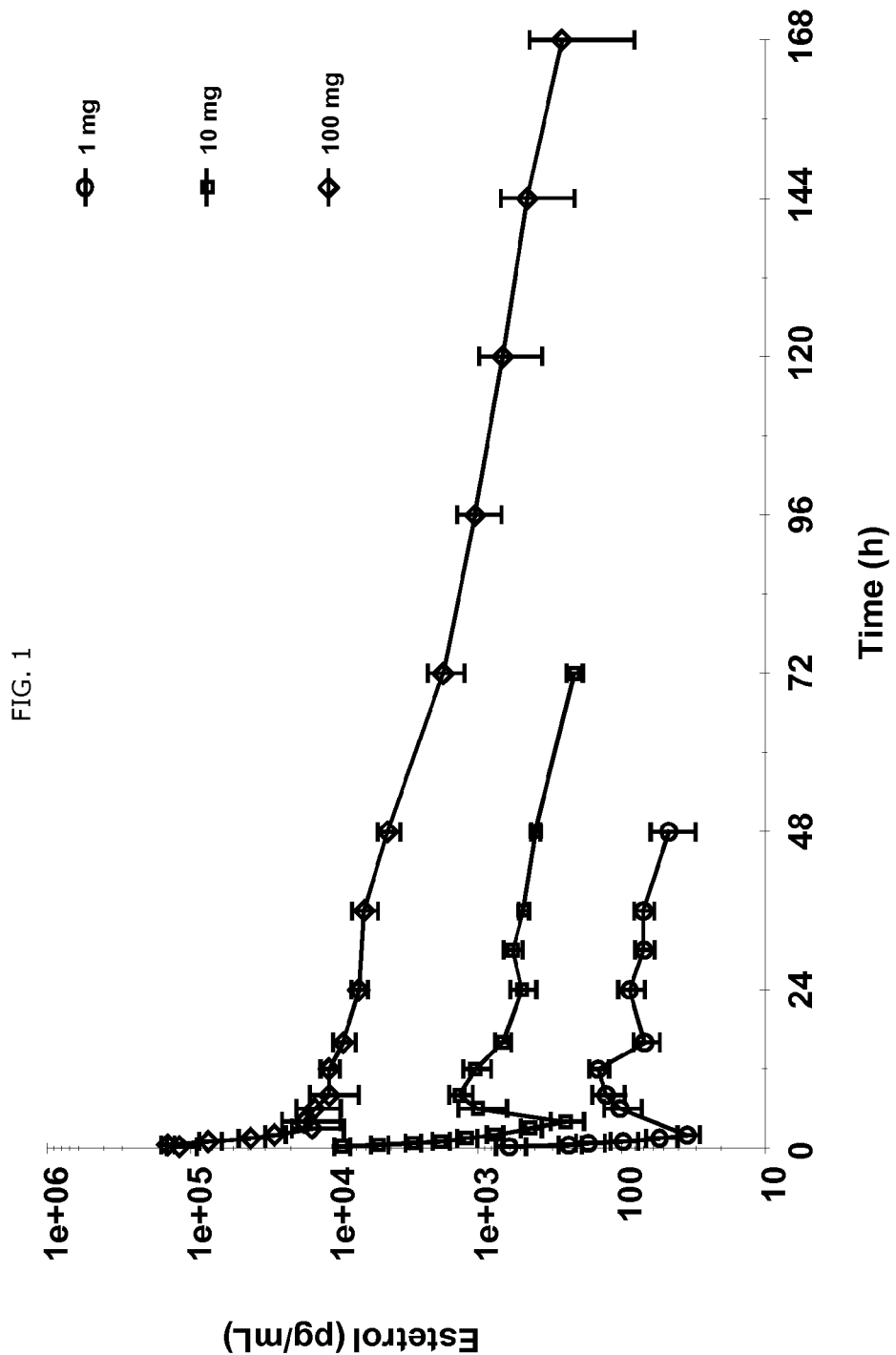
FIG. 1 provides the mean estetrol plasma levels (±standard error) of healthy post-menopausal women that were orally administered a single dose of 1, 10 or 100 mg estetrol.

The terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. Where embodiments are referred to as "comprising" particular features, elements or steps, this is intended to specifically include embodiments which consist of the listed features, elements or steps.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

All documents cited in the present specification are hereby incorporated by reference in their entirety.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

The present inventors have found that emergency contraception can be provided by administration of a single dose of a tetrahydroxylated estrogen, preferably estetrol. They have found that estetrol can inhibit ovulation in rats and prevent pregnancy in rabbits. Furthermore, they have shown that estetrol has an inhibitory effect on gonadotropins (luteinizing hormone and follicle stimulating hormone) in early post-menopausal women that were orally administered a single dose of estetrol. In addition, estetrol was shown to have a high oral bioabsorption and a remarkably long elimination half-life.

Accordingly, one aspect of the present invention relates to the use of a tetrahydroxylated estrogen, preferably estetrol as an emergency contraception or in a method of emergency contraception.

"Emergency contraception" is defined herein as a treatment aimed at preventing pregnancy after sexual intercourse. In contrast to a normal contraceptive, which is administered daily in a low dose during the ovulation cycle, an emergency contraceptive is generally administered in a single (or double) high dose. "Pregnancy" refers in this context to the condition of a female after a fertilized ovum has successfully implanted itself in the lining of the uterus.

"Estetrol", "1,3,5(10)-estratrien-3, 15α, 16α, 17β-tetrol" and "$E_4$" are synonyms and are used interchangeably herein to refer to a natural estrogen, produced by the human fetal liver during pregnancy only. Structurally, it is characterized by the presence of four hydroxyl groups, hence its acronym $E_4$. Estetrol has been proposed for hormone replacement therapy, contraception, prevention of osteoporosis and treatment of breast cancer, but never for use as an emergency contraceptive. Estetrol is a so-called "tetrahydroxylated estrogen" and also encompasses derivatives, such as those represented by the general formula (I):

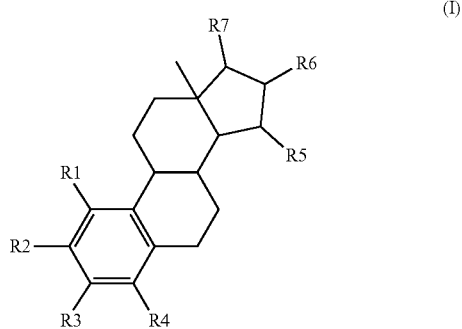

(I)

wherein R1, R2, R3, R4 independently are a hydrogen atom, a hydroxyl group, an alkoxy group with 1-5 carbon atoms, or a keto group;
wherein each of R5, R6, R7 is a hydroxyl group; and
wherein no more than 3 of R1, R2, R3, R4 are hydrogen atoms.

In a preferred embodiment, said tetrahydroxylated estrogen is estetrol having the following formula (II):

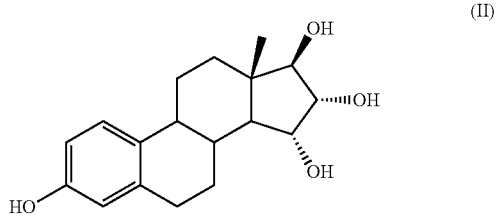 [SMILES: C[C@]12CCC3c4ccc(O)cc4CCC3C1[C@@H](O)[C@@H](O)[C@@H]2O]

(II)

Because of the remarkably long elimination half-life of estetrol, the emergency contraceptive of the present invention may be administered in a single dose. However, also encompassed herein is the administration of multiple doses, e.g. two doses, taken for instance 12 hours apart.

When used in humans, good results can be obtained with a single oral dose of between 30 mg and 400 mg, such as between 40 mg and 250 mg, between 40 mg and 200 mg, between 40 mg and 150 mg, between 40 mg and 100 mg, or between 50 mg and 100 mg of the tetrahydroxylated estrogen, preferably estetrol.

Alternatively, the single dose of the tetrahydroxylated estrogen, preferably estetrol, can be determined in view of the body weight of the subject to which it needs to be administered. Typical doses are those in the following ranges: 0.5 to 7.0 mg/kg, 1.0 to 5.0 mg/kg, 1.5 to 2.5 mg/kg, or about 2.0 mg/kg. A dose of 0.5 mg/kg thus corresponds to a dose of 30 mg for a subject with a body weight of 60 kg, while a dose of 4 mg/kg corresponds to a dose of 240 mg/kg for a subject with a body weight of 60 kg, etc.

In a preferred embodiment, emergency contraceptive of the present invention can be administered orally for use as emergency contraceptive. Advantageously, the inventors have found that after oral intake a high and fast peak level of estetrol is observed in the plasma. Hence, immediate effects can be obtained after oral administration of estetrol. Oral dosage forms are well known to those skilled in the art and can be, for example, tablets, film-coated tablets, coated tablets, capsules, gel caps, pills or powder preparations. Besides the active ingredient estetrol, the dosage forms according to the present invention further comprise a pharmaceutically acceptable excipient such as, for example, but not limited to, lactose, starch, polyvinylpyrrolidone (PVP), magnesium stearate etc.

Alternatively, the emergency contraceptive of the present invention can also be administered through parenteral, rectal, vaginal, transcutaneous or topical administration.

In a preferred embodiment, the emergency contraceptive of the present invention is administered non-vaginally. In another embodiment, the emergency contraceptive of the present invention can also be administered through parenteral, rectal, transcutaneous or topical administration.

Also disclosed herein are dosage forms which further comprise another active ingredient or an excipient which has a certain activity.

Another aspect of the present invention relates to a pharmaceutical composition comprising between 0.5 mg/kg and 7 mg/kg estetrol, as active ingredient and a pharmaceutically acceptable excipient.

The emergency contraceptive of the present invention is administered within a limited period of time following sexual intercourse and preferably as soon as possible after sexual intercourse. Usually this time period is within 120 hours (5 days) of intercourse, such as within 96 (4 days), 72 (3 days), 48 (2 days), 24 hours (1 day) of sexual intercourse, or less.

The results obtained by the present invention indicate that E4 in rabbits prevents pregnancies with a high efficiency. Without wanting to be bound by any theory, E4 can be used up to 120 hours after the intercourse, which provides an advantage over known emergency pills. Estetrol has been shown herein to prevent ovulation and prevent pregnancies. Estetrol is effective even when administered shortly before ovulation when the LH surge has already started to rise, a time period when use of e.g. levonorgestrel is no longer effective, or even after ovulation, when none of the existing emergency pills are effective.

The inventors have shown that single doses up to 100 mg tetrahydroxylated estrogen, preferably estetrol are safe and well tolerated in humans, which is an advantage over synthetic estrogens such as ethinyl estradiol, which are associated with undesirable side-effects such as thromboembolism, fluid retention, nausea, bloating, cholelithiasis, headache and breast pain.

Another aspect of the present invention relates to a method of emergency contraception, which method comprises the oral administration of a single dose of tetrahydroxylated estrogen, preferably estetrol of between 0.5 and 7 mg/kg to a female within 120 hours of sexual intercourse.

Further disclosed herein is a dosage regimen for emergency contraception using tetrahydroxylated estrogen, preferably estetrol as active ingredient. The dosage regimen according to the present invention is that a single dose of between 0.5 and 7 mg/kg of tetrahydroxylated estrogen, preferably estetrol as active ingredient is administered within 120 hours of sexual intercourse.

Alternatively, said dosage regimen can be applied in two consecutive phases, with e.g. an interval of 6, 12, 18, or 24 hours.

Also disclosed herein is an emergency contraceptive kit comprising a pharmaceutical composition comprising tetrahydroxylated estrogen, preferably estetrol as defined herein. The kit may further comprise instructions for use.

The present invention is further illustrated by the following examples, which do not limit the scope of the invention in any way.

EXAMPLES

Example 1

Anti-Ovulatory Effect of E4 in Four-Day Cyclic Rats

The present example demonstrates the antiovulatory activity of estetrol ($E_4$) after oral administration in four-day cyclic rats.

Vaginal smears from female rats were obtained daily for two weeks prior to the start of treatment to identify four-day cycling rats. All treatments were administered orally twice daily at approximately 6:30 am and 4:30 pm for four consecutive days (Days 1-4), starting on the day of estrus. One day after the final dose (Day 5), the rats were euthanized by $CO_2$ asphyxiation at approximately 1 pm, and the number of ova per oviduct was counted by visualization under a dissecting microscope and recorded.

In one study, animals (8 per group) were treated with $E_4$ (0.03; 0.1; 0.3; 1.0 or 3.0 mg/kg) or ethinylestradiol (EE) (0.0003; 0.001; 0.003, 0.01 or 0.03 mg/kg). The control group was given the vehicle only.

All rats ovulated when treated p.o. with the vehicle whereas animals receiving $E_4$ or EE showed a decrease of the ovulatory activity. $E_4$ treatment at twice daily doses of 0.03 mg/kg did not inhibit ovulation. At the higher doses, $E_4$ blocked ovulation in a dose-related fashion. Ovulation was inhibited in 2 of 8 rats at twice daily $E_4$ doses of 0.1 mg/kg; in 5 of 8 rats at 0.3 mg/kg; in 7 of 8 rats at 1.0 mg/kg and in 8 of 8 rats at 3.0 mg/kg. The calculated $ED_{50}$ was 0.182 mg/kg. Twice daily treatment with EE produced the following responses: 0.0003 mg/kg and 0.001 mg/kg did not inhibit ovulation; 0.003 mg/kg blocked ovulation in 1 of 8 rats; 0.01 mg/kg in 4 of 8 rats; and 0.03 mg/kg in 8 of 8 rats. The calculated $ED_{50}$ was 0.01 mg/kg.

The results of this study show that $E_4$, as well as EE, displays an antiovulatory activity under these experimental conditions.

In another study, the antiovulatory activity of $E_4$ was evaluated relative to that of estradiol ($E_2$). Animals (8 per group) were treated with $E_4$, $E_2$ or vehicle (control group). Due to the steepness of the dose-response curve, the antiovulatory $ED_{50}$ for $E_2$ could not be calculated, but was found to be in the range of 0.03 to 0.1 mg/kg. The antiovulatory $ED_{50}$ for $E_4$ was estimated as being 0.204 mg/kg.

The results of this study show that $E_4$, as well as $E_2$, displays an antiovulatory activity under these experimental conditions.

In conclusion, the studies demonstrated that $E_4$ suppressed ovulation when given orally to adult cyclic rats.

Example 2

Prevention of Pregnancy in Rabbits

In the present example it was assessed whether $E_4$ can prevent pregnancy in rabbits.

Eighteen proven fertile female rabbits, 3 per group were dosed twice daily at approximately 12 hour intervals for 14 days starting four days before mating:

Group 1: vehicle control (ASV: 0.9% sodium chloride, 0.4% polysorbate 80, 0.5% carboxymethylcellulose and 0.9% benzyl alcohol in distilled or deionised water, 1 ml/kg), Group 2: 0.01 mg/kg $E_4$ in ASV, 1 ml/kg, Group 3: 0.03 mg/kg $E_4$ in ASV, 1 ml/kg, Group 4: 0.1 mg/kg $E_4$ in ASV, 1 ml/kg, Group 5: 0.3 mg/kg $E_4$ in ASV, 1 ml/kg and Group 6: 1.0 mg/kg $E_4$ in ASV, 1 ml/kg. Doses were determined by body weights taken the first day of dosing and were adjusted according to weights obtained one week later. Each female rabbit was bred with two proven fertile male rabbits after four days of dosing. The females were necropsied ten days later and the number of pregnancies were determined.

The results of the study are given in Table 1. In the vehicle control group a total of 25 ovulations were observed. Inhibition of ovulation was clearly present in the 1.0 mg/kg dose group where only 3 ovulations were seen. Enlarged uteri in the rabbits with no corpora lutea confirmed successful copulation. In the vehicle treated group a total number of 13 pregnancies were observed resulting from 15 ovulations (2 animals). At the dose of 0.1 mg/kg no pregnancies were observed, although 20 ovulations occurred. Similarly, at the dose of 0.3 mg/kg 20 ovulations occurred, but no pregnancies were seen.

TABLE 1

Effects of vehicle control and different doses of $E_4$ on ovulation and pregnancy

| | N corpora lutea | | N pregnancies | |
| --- | --- | --- | --- | --- |
| | Individual values (3 animals per group) | Total number | Individual values (3 animals per group) | Total number |
| Vehicle control | 10; 7; 8 | 25 | 0; 7; 6[1] | 13 |
| 0.01 mg/kg | 13; 9[2] | 22 | 13; 9[2] | 22 |
| 0.03 mg/kg | 5; 6; 11 | 22 | 5; 5; 11 | 21 |
| 0.1 mg/kg | 5; 7; 8 | 20 | 0; 0; 0 | 0 |

TABLE 1-continued

Effects of vehicle control and different
doses of $E_4$ on ovulation and pregnancy

| | N corpora lutea | | N pregnancies | |
|---|---|---|---|---|
| | Individual values (3 animals per group) | Total number | Individual values (3 animals per group) | Total number |
| 0.3 mg/kg | 6; 7; 7 | 20 | 0; 0; 0 | 0 |
| 1.0 mg/kg | 0; 0; 3 | 3 | 0; 0; 0 | 0 |

[1]One vehicle control female had no pregnancies.
[2]One female failed to breed.
It is concluded that oral doses of $E_4$ higher than 0.3 mg/kg b.i.d. induce inhibition of ovulation. Dosages above 0.03 mg/kg b.i.d. caused complete prevention of pregnancy.

Example 3

Effects of E4 on the Pregnancy of the Wistar Rat

The objective of the present studies was to assess the effects of $E_4$ on the pregnancy of the Wistar rat when administered orally by gavage.

In one study, groups of seven mated female rats were given $E_4$ orally, by gavage, at dose levels of 30, 60 or 90 mg/kg/day from Day 6 to 17 of gestation inclusive. A similar group of seven rats was given the vehicle, 0.5% w/v carboxymethylcellulose, over the same period to act as controls. On Day 20 of gestation, the females were examined.

There were no deaths during the study; all animals survived until scheduled necropsy. There were no relevant unexpected clinical observations or necropsy findings recorded that were considered to be related to treatment. Group mean body weight loss and a marked reduction in mean food intake was observed in all dose groups for the treatment period.

In another study, using the same protocol as the study above, groups of seven mated female rats were given $E_4$ at dose levels of 0.1, 0.3, 1, 3 and 10 mg/kg/day or vehicle (controls).

There were no deaths during the study. Three females in the group receiving 10 mg/kg/day and one female in the group receiving 3 mg/kg/day were observed to be hunched towards the end of the gestation period. There were no other clinical observations recorded that were considered to be related to treatment. At 10 mg/kg/day, there was an overall loss in mean body weight during the treatment period, with reduced mean food intake. At 0.1, 0.3, 1 and 3 mg/kg/day, mean body weight gains were less than the controls over the treatment period, with a reduction in mean gravid uterus weight in the groups receiving 0.3, 1 and 3 mg/kg/day. At 1 and 3 mg/kg/day, mean food intake over the treatment period was slightly lower than the control.

At a dose level below 3 mg/kg/day, only slight maternal toxicity was observed.

Example 4

Toxicity Study of Estetrol in Monkeys

A maximum tolerated dose (MTD) study was performed in adult female cynomolgus monkeys.

Three control animals were treated orally with vehicle, and four other animals were treated orally with $E_4$ as a suspension in vehicle at single increasing doses of 1, 10, 100 or 1000 mg/kg on days 1, 3, 6 and 14 respectively.

There were no unscheduled deaths during the conduct of the study.

There were no major clinical signs related to the $E_4$ treatment. The only adverse clinical sign observed was emesis in one $E_4$-treated animal at the 1000 mg/kg dose, approximately 12 h after dosing.

No effects on body weight or on haematological parameters were observed.

Clinical chemistry showed decreased levels of inorganic phosphorus in 2 of 3 control animals and in 3 of 4 of the 1-mg/kg $E_4$-treated animals the day after dosing. Afterwards decreased levels were observed in all $E_4$-treated animals after the 100 mg/kg dose and in one control animal and all $E_4$-treated animals after the 1000 mg/kg dose. This finding is probably of minor relevance.

Minor findings in some liver parameters (aspartate aminotransferase (AST) and alanine aminotransferase (ALT)) were observed in one control animal and in one $E_4$-treated animal. However, no apparent test item- or dose-related findings were evident.

Gross necropsy did not reveal any unusual findings.

It is concluded that single oral treatment of cynomolgus monkeys with $E_4$ up to doses of 1000 mg/kg was well tolerated and did not reveal any relevant toxicological finding.

Example 5

Safety, Tolerability, Pharmacokinetics and Pharmacodynamics of a Single Dose of E4 in Healthy Post-Menopausal Women In the present example the safety, tolerability, pharmacokinetics and pharmacodynamics of a single escalating dose of $E_4$ (0.1, 1, 10 and 100 mg) was evaluated in healthy postmenopausal women.

A double-blind, randomized, placebo-controlled, single rising dose study (0.1, 1, 10 and 100 mg of $E_4$) was performed in healthy postmenopausal women. 32 healthy postmenopausal female volunteers between 53 and 69 years of age were enrolled. Menopause was defined as ≥12 months amenorrhea or 6 months amenorrhea with serum FSH levels≥40 IU/l and serum $E_2$<73 pmol/l. The treatment groups were comparable with respect to the demographic parameters and characteristics. A total of 8 subjects were assigned to each dose group; six subjects received active treatment and two subjects received placebo.

Safety

No severe or serious adverse events were reported. One adverse event was of moderate intensity (back pain, classified as not related), all others were mild. One notable adverse event (AE) was reported in a subject of the highest dose group (100 mg $E_4$): an allergic reaction (urticaria), which was considered as not serious, mild and probably related to $E_4$. The subject recovered completely within several hours. Post study allergy tests failed to confirm a direct allergic response to $E_4$ or the test solution used in the study. The most frequently observed AEs occurred in the system organ classes Nervous System Disorders and Gastrointestinal Disorders in subjects in all dosing groups including placebo treated subjects (see Table 2). The number and nature of AEs was similar in subjects on placebo and on 0.1, 1.0 and 10 mg $E_4$. The number of AEs (all AEs and related AEs) was highest in the subjects on 100 mg $E_4$. No cumulation of specific AEs was observed in any treatment group. The number of subjects reporting AEs was comparable between the treatment groups with the lowest number in the 10 mg group, in which just one AE occurred. There were no notable changes in ECGs, any of the laboratory tests or vital signs.

B100 were noticed. Minimal changes were observed in the bone parameters osteocalcin and C-telopeptide. No relevant changes were observed in the clotting parameters Factor XII

TABLE 2

Drug-related adverse events, reported by more than one subject in any dose-group

| System Organ Class | Placebo (N = 8) | | | 0.1 mg (N = 6) | | | 1 mg (N = 6) | | | 10 mg (N = 6) | | | 100 mg (N = 6) | | |
|---|---|---|---|---|---|---|---|---|---|---|---|---|---|---|---|
| Preferred Term | E | n | % | E | n | % | E | n | % | E | n | % | E | n | % |
| Gastrointestinal disorders | | | | | | | | | | | | | | | |
| Diarrhoea NOS | 1 | 1 | 12.5 | — | | | — | | | — | | | 2 | 2 | 33.3 |
| Musculoskeletal and connective tissue disorders | | | | | | | | | | | | | | | |
| Myalgia | — | | | — | | | — | | | 1 | 1 | 16.7 | 2 | 2 | 33.3 |
| Nervous system disorders | | | | | | | | | | | | | | | |
| Somnolence | — | | | 1 | 1 | 16.7 | 1 | 1 | 16.7 | — | | | 2 | 2 | 33.3 |

N = number of subjects per treatment group
E = number of adverse events
n = number of subjects with adverse events
% = percentage of subjects with adverse events per number of subjects per treatment group
In conclusion, the results of this study showed that $E_4$ after single administration at a dose up to 100 mg is safe and well tolerated.

Pharmacokinetics

The mean plasma $E_4$ concentrations versus time plots of the 1 mg, 10 mg and 100 mg group are presented in FIG. 1. Plasma concentration profiles could not be determined in subjects of the 0.1 mg group.

The pharmacokinetic data of $E_4$ were very consistent within each dose group and throughout the dose range studied. Inter-subject variability was very low.

The absorption of $E_4$ was extremely fast and followed by fast redistribution. Reabsorption was evident during the first 18 h after oral intake. The compound was eliminated with a terminal half life of 28 hours (ranges 18-60 h).

$AUC_{0-\infty}$ values were proportional to the oral dose in the range from 10 to 100 mg $E_4$.

$C_{max}$ values were proportional in the range from 1 to 100 mg $E_4$. The terminal half life and fractional clearance values were not affected by dose level.

In conclusion, the results of the present study show that, in the dose range tested, $E_4$ has a high and dose-proportional oral bioabsorption with a consistent plasma profile due to little interindividual variation, and a remarkably long terminal elimination half-life of about 28 hours.

Pharmacodynamics

Figure 2:
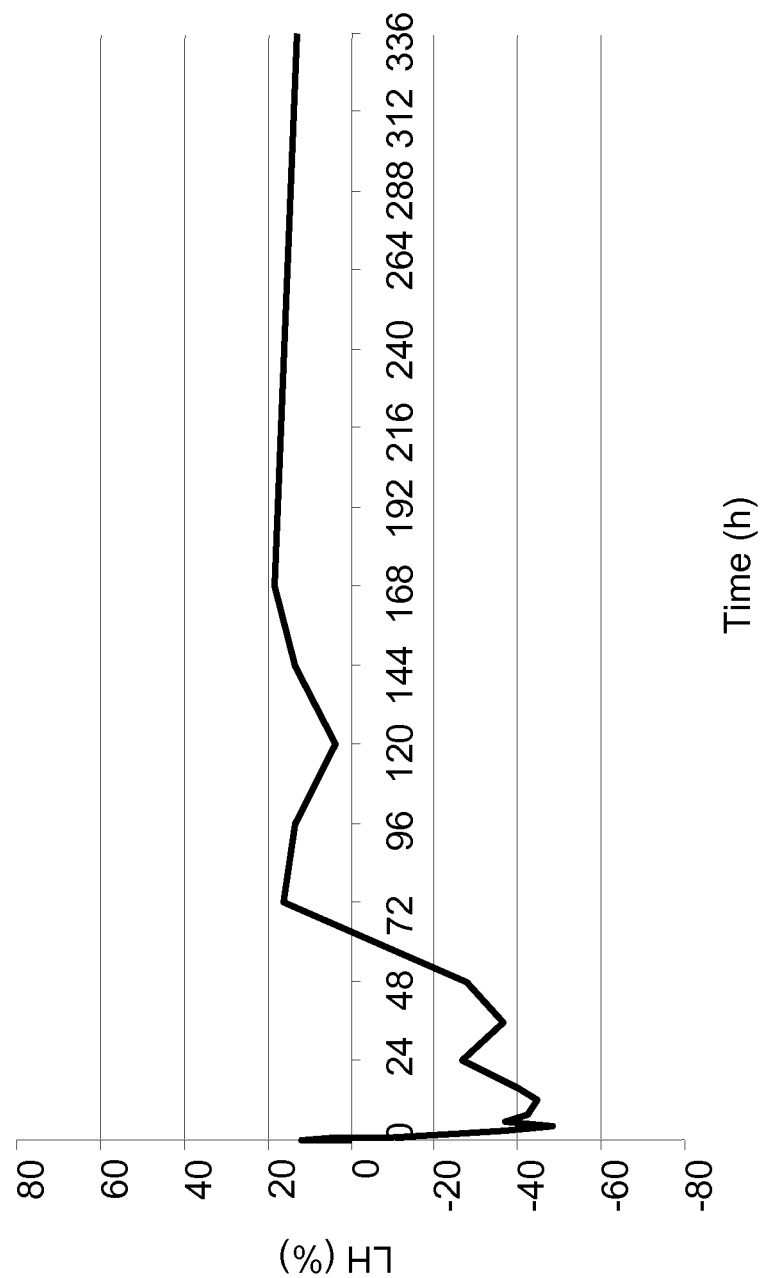
FIG. 2 provides the percentage change of the mean luteinizing hormone (LH) levels in post-menopausal women that received a single oral dose of 100 mg estetrol.

The pharmacodynamic data showed a clear dose-dependent inhibition of plasma LH levels by $E_4$ up to 48 hours after dosing. The maximum mean suppression was 48% at 4 hours after dosing. A second LH trough of 45% is seen at 12 hours after dosing, synchronous with the mean $E_4$ levels. The percentage change of the LH levels of the 100 mg group are shown in FIG. 2.

Figure 3:
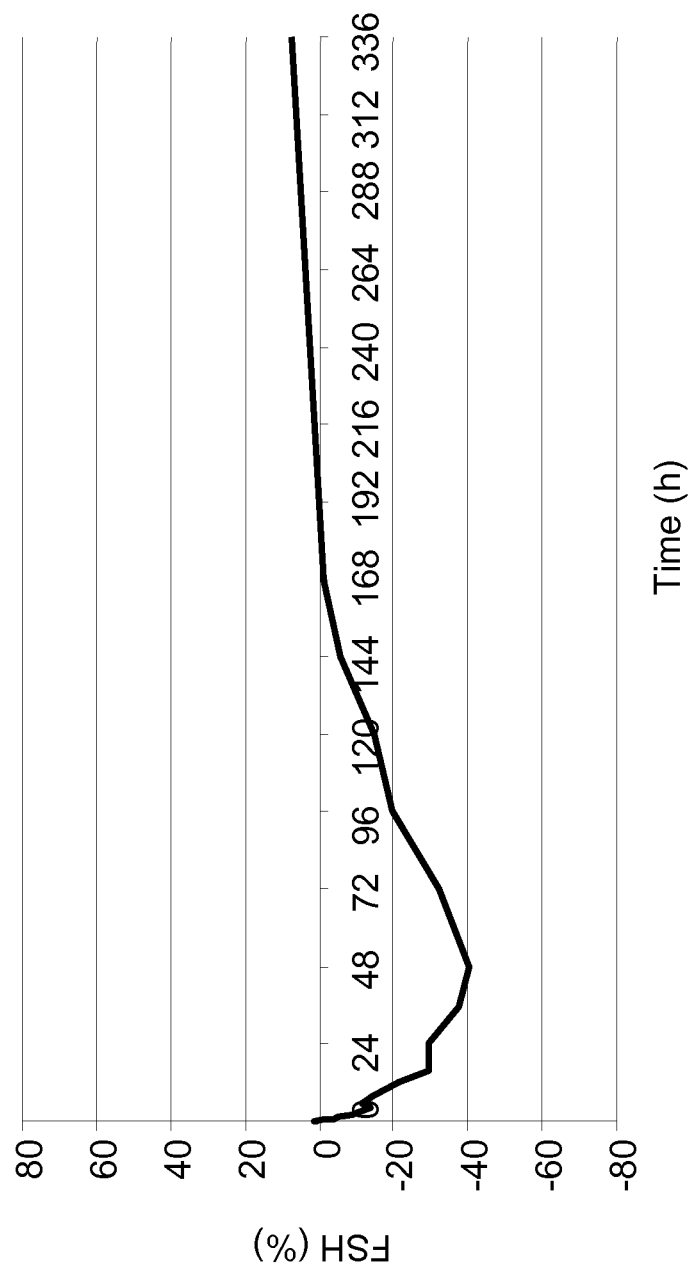
FIG. 3 provides the percentage change of the mean follicle stimulating hormone (FSH) levels in post-menopausal women that received a single oral dose of 100 mg estetrol.

A profound and sustained inhibition of FSH levels, with a maximum suppression of 41% at 48 hrs after dosing, could also be established in the 100 mg dose group (not measured in the other dosing groups) up to 168 hours (1 week) after dosing. The percentage change of the FSH levels of the 100 mg dose group is presented in FIG. 3.

Some fast reacting, estrogen-sensitive parameters related to hepatic and bone metabolism were determined in the 100-mg dose group only. A slight increase in triglycerides and a slight decrease in LDL-cholesterol and apolipoproteinand plasminogen. A slight increase in SHBG and CBG was observed. The overall profile suggests minimal effect on liver metabolism. Interpretation of the pharmacodynamic data must be made with care taking into consideration the small number of subjects and the single dose administration.

No significant endometrial stimulation occurred as none of the subjects experienced a withdrawal bleeding after discontinuation of progestogen post treatment.

In conclusion, the effects of $E_4$ on LH and FSH levels denote a strong central gonadotropin inhibiting potency of the compound.

Example 6

Ovulation Inhibition Study of Estetrol in Healthy Women with a Regular Menstrual Cycle The present example shows the inhibition of ovulation with a single dose of estetrol after oral administration in healthy women with a regular menstrual cycle.

A randomized, double-blind, placebo-controlled cross-over study is performed in healthy women with a regular menstrual cycle. The women do not use a hormonal contraceptive and a regular menstrual cycle is defined as a menstrual cycle of between 24-35 days. The women are randomized to one of the treatment groups, a total of 20 women are assigned to each treatment group. In each treatment group, each women receives one oral dose of estetrol (e.g. 50 mg, 75 mg or 100 mg of estetrol) in one treatment cycle and one oral dose of placebo in another treatment cycle (cross-over).

The subjects are first screened in a pre-treatment cycle (i.e. a normal menstrual cycle) to investigate the follicle development and to confirm ovulation. Follicular development and endometrium are measured by transvaginal ultrasound (TVUS) every 3 days starting on day 6 of the menstrual cycle until ovulation is observed. When a follicle diameter of 13 mm is measured, the subjects are seen every second or every day. An ovulation is considered to be confirmed if a serum progesterone (P) value≥16 nmol/L is measured. Luteal phase should be at least 10 days.

In a treatment cycle, follicular development and endometrium are measured by TVUS every 3 days starting on day 6 of the menstrual cycle until the leading follicle is ≥18 mm. When a follicle diameter of 13 mm is measured, the subjects are seen every second or every day. Subjects are treated (with a single oral dose of estetrol or placebo) when the leading follicle is ≥18 mm. Following treatment, the subject is followed up for 6 days by daily TVUS and collection of blood samples for measuring hormone levels (FSH, LH, E2, P). In case the follicle has already been ruptured, the subject is still treated.

Example 7

Efficacy, Safety and Tolerability of Estetrol in Comparison to Levonorgestrel for Emergency Contraception in Healthy Women of Reproductive Age The present example shows the efficacy, safety and tolerability of estetrol in comparison to levonorgestrel (LNG) for emergency contraception in healthy women of reproductive age.

A prospective, randomized, double-blind, multicenter, active controlled study is performed in healthy women of reproductive age with a regular menstrual cycle who present themselves for emergency contraception within 48 to 120 h after unprotected intercourse. The women are at least 18 years, do not use hormonal contraception and a regular menstrual cycle is defined as a menstrual cycle of between 24-35 days. The women are randomized to receive between 48 h and 120 h after unprotected intercourse a one-time treatment with either one dose of 50 to 100 mg E4 or one dose of 1.5 mg of LNG with follow-up visits at 5-7 days after expected onset of menses and another visit at 12-14 days after expected onset of menses (if needed). 40-45 women per clinical site are participating in the study, with a total of 40-45 clinical sites.

Post-treatment pregnancy rates are compared between the treatment groups. Pregnancy (efficacy) is determined by detecting the pregnancy hormone human chorionic gonadotropin (hCG) in the serum and return of menstruation.

Menstrual bleeding patterns are evaluated until follow-up about one week after next menses.

Safety and tolerability are evaluated by determination of routine safety laboratory parameters (haematology, biochemistry and urinalysis), vital signs, by performing physical, gynaecological and breast examinations, blood pressure, heart rate, body weight, and by monitoring (serious) adverse events until follow-up about one week after next menses.

The invention claimed is:

1. A method of emergency contraception in a mammalian female
comprising the administration to a female in need of an emergency contraceptive comprising, as the sole active ingredient for inhibiting ovulation and pregnancy, tetrahydroxylated estrogen represented by the general formula (I):

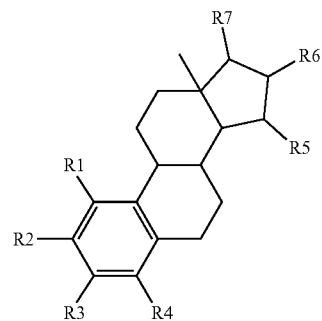

wherein R1, R2, R3, R4 independently are a hydrogen atom, a hydroxyl group, or an alkoxy group with 1-5 carbon atoms;
wherein each of R5, R6, R7 is a hydroxyl group; and
wherein no more than 3 of R1, R2, R3, R4 are hydrogen atoms, in an effective amount to inhibit ovulation and pregnancy in the female.

2. The method according to claim 1, wherein said administration is performed through non-vaginal administration.

3. The method according to claim 1, wherein said administration is performed through oral, parenteral, rectal, transcutaneous or topical administration.

4. The method according to claim 1, wherein said emergency contraceptive additionally comprises a pharmaceutically acceptable salt of said tetrahydroxylated estrogen or excipient.

5. The method according to claim 1, wherein said tetrahydroxylated estrogen is estetrol (1,3,5(10)-estratrien-3, 15α, 16α 17β-tetrol).

6. The method according to claim 1, wherein said emergency contraceptive comprises the tetrahydroxylated estrogen in a dose of between 0.5 and 7 mg/kg, between 1.0 to 5.0 mg/kg, between 1.5 to 2.5 mg/kg, or of about 2.0 mg/kg.

7. The method according to claim 1, wherein said emergency contraceptive comprises the tetrahydroxylated estrogen in a dose of between 30 mg and 400 mg, between 40 mg and 250 mg, between 40 mg and 200 mg, between 40 mg and 150 mg, between 40 mg and 100 mg, between 50 mg and 100 mg of estetrol, or of about 100 mg.

8. The method according to claim 1, wherein the administration is performed in a single dosage.

9. The method according to claim 1, wherein the administration is performed in a double dosage.

10. The method according to claim 1, wherein said administration is performed within 120 hours after sexual intercourse.

11. The method according to claim 1, wherein said administration is performed within 96, 72, 48, 24, 12 hours or less after sexual intercourse.

12. The method according to claim 1, wherein the administration is performed in a double dosage with an interval of 6, 12, 18, or 24 hours.

* * * * *

UNITED STATES PATENT AND TRADEMARK OFFICE
CERTIFICATE OF CORRECTION

PATENT NO. : 9,579,329 B2  
APPLICATION NO. : 14/238310  
DATED : February 28, 2017  
INVENTOR(S) : Wout Wouters et al.

Page 1 of 1

It is certified that error appears in the above-identified patent and that said Letters Patent is hereby corrected as shown below:

On the Title Page

Under Item (73) Assignee, please delete "Estetra S.P.R.L., Bierset (BE)" and replace with --Estetra S.P.R.L., Liege (BE)--

Signed and Sealed this
Twenty-second Day of January, 2019

Andrei Iancu
*Director of the United States Patent and Trademark Office*